(12) United States Patent
Kim

(10) Patent No.: US 6,849,054 B1
(45) Date of Patent: Feb. 1, 2005

(54) LIE-DOWN MASSAGER

(76) Inventor: Hakjin Kim, 610 Ridgeview Ct., Diamond Bar, CA (US) 91765

( * ) Notice: Subject to any disclaimer, the term of this patent is extended or adjusted under 35 U.S.C. 154(b) by 10 days.

(21) Appl. No.: 10/623,955

(22) Filed: Jul. 21, 2003

(51) Int. Cl.[7] ............................ A61H 7/00; A61H 15/00
(52) U.S. Cl. ........................... 601/98; 601/15; 601/100; 601/101; 601/103; 601/116
(58) Field of Search .............................. 601/15, 18, 19, 601/86, 87, 90, 92, 94, 95, 98–103, 115, 116, 118, 122, 126; 606/240, 241, 242

(56) References Cited

U.S. PATENT DOCUMENTS

| | | | |
|---|---|---|---|
| 2,193,882 A | | 3/1940 | Petersen |
| 2,310,106 A | | 2/1943 | Miller |
| 2,359,933 A | | 10/1944 | Niblack |
| 2,781,040 A | | 2/1957 | Hill |
| 2,874,689 A | | 2/1959 | Gavelek |
| 2,909,173 A | | 10/1959 | Anderson |
| 3,687,133 A | | 8/1972 | Grubelic |
| 3,877,422 A | | 4/1975 | Heuser et al. |
| 4,190,043 A | | 2/1980 | Thompson |
| 4,422,449 A | * | 12/1983 | Hamabe ........................ 601/99 |
| 4,458,675 A | | 7/1984 | Nakao et al. |
| 4,586,493 A | | 5/1986 | Goodman |
| 4,656,998 A | | 4/1987 | Masuda et al. |
| 4,899,403 A | | 2/1990 | Yamasaki |
| 4,947,833 A | | 8/1990 | Yamasaki |
| 5,038,757 A | | 8/1991 | Yamasaki |
| 5,088,475 A | | 2/1992 | Steffensmeier |
| 5,165,390 A | | 11/1992 | Fleetwood |
| 5,179,940 A | * | 1/1993 | Barreiro ........................ 601/99 |
| 5,755,677 A | | 5/1998 | Masuda et al. |
| 5,807,288 A | | 9/1998 | Wu |
| 6,071,252 A | | 6/2000 | Marcantoni |
| 6,190,338 B1 | | 2/2001 | Arndt |
| 6,224,563 B1 | | 5/2001 | Nonoue et al. |
| 6,243,609 B1 | | 6/2001 | Lee |
| 6,409,689 B1 | | 6/2002 | Chen |
| 6,454,732 B1 | | 9/2002 | Lee |
| 6,542,779 B1 | | 4/2003 | Lee |
| 6,555,798 B1 | | 4/2003 | Lee |
| 6,629,939 B2 | * | 10/2003 | Jikiba et al. .................. 601/99 |
| 6,643,551 B1 | * | 11/2003 | Park ........................... 607/100 |
| 2002/0138023 A1 | | 9/2002 | Kume et al. |
| 2002/0193713 A1 | | 12/2002 | Lee |
| 2003/0018284 A1 | | 1/2003 | Lim |

* cited by examiner

Primary Examiner—Michael A. Brown
Assistant Examiner—Quang Thanh
(74) Attorney, Agent, or Firm—Park & Sutton LLP; John K. Park

(57) ABSTRACT

A lie-down massager comprises a base frame having a top panel with a top opening formed centrally and lengthwisely through the top panel, a rider provided below the top panel to make a horizontally reciprocal movement relative to the base frame, a lifter liftedly engaged to the rider to make a vertically reciprocal movement relative to the rider, a massage member fixed downwardly to the lifter with supports horizontally aligned along a top portion of the massage member, massage bumps attached atop the first and second supports, and a pad covering the massage bumps and the elongated opening of the base frame. The supports repeatedly approach to and distance from each other within the top opening.

24 Claims, 5 Drawing Sheets

LIE-DOWN MASSAGER

BACKGROUND OF THE INVENTION

The invention relates generally to a massaging device. More particularly, the present invention relates to an improved lie-down massager capable of efficiently treating bodily malfunctions such as back pain and gastrointestinal weakness by applying a therapeutic massaging treatment along the back and neck of a patient lying down on the massager whose massaging bumps move horizontally and vertically along the patient's spinal cord and neck in which the vertical movement of the massaging bumps optimally coordinates with a widthwise reciprocation to repeatedly approach to and distance from each other.

Conventional bed or mat type massaging devices employ a spring mechanism for vertically moving massaging bumps. As disclosed U.S. Pat. No. 6,454,732, a spring mechanism allows the massaging bumps to gently move up and down. However, when it comes to therapeutic effects, the spring mechanism proves too soft to push up the massaging bumps when stronger pressure is required, because tension of springs applies equally to patients lying on the massaging device regardless of patient's requirements.

A demand is to adopt a reliable mechanism demonstrating a steady and robust therapeutic effects while harmonizing the vertical movement with a widthwise reciprocation between the massaging bumps.

SUMMARY OF THE INVENTION

The present invention is contrived to overcome the conventional disadvantages. Accordingly, an object of the invention is to provide a lie-down massager that improves therapeutic effects by harmonizing a vertical reciprocation with a widthwise reciprocation of massage bumps.

Another object is to optimize spinal and neck massage effects by allowing the massage bumps to repeatedly become near to and away from each other, thereby enabling patients to receive a widespread massage along the backs and necks of the patients. A further object is to improve product reliability and customer satisfaction by reliably synthesizing vertical, lengthwise and widthwise reciprocations of the massage bumps.

To achieve these and other objects, the lie-down massager according to the present invention comprises a base frame having an elongated top panel with an elongated top opening formed centrally and lengthwisely through the elongated top panel. A rider is provided below the elongated top panel of the base frame to make a horizontally reciprocal movement relative to the base frame, and a lifter liftedly engaged to the rider to make a vertically reciprocal movement relative to the rider. A massage member is fixed downwardly to the lifter, and first and second supports are horizontally aligned along a top portion of the massage member. Another member is also provided for allowing the first and second supports to repeatedly approach to and distance from each other within the elongated opening. Here, massage bumps attached atop the first and second supports, and a pad covering the massage bumps and the elongated opening of the base frame.

In an embodiment, a pair of pulleys are linked by a rope and respectively mounted in a front end portion and a rear end portion of the base frame so that a predetermined portion of the rope is fixedly attached to the rider. In this construction, the pulley rotation enables the rider to generate a horizontally reciprocal movement along the elongated top opening. Alternately, there may be provided a pair of rack gears parallel to each other and provided below the elongated top panel where a rider is provided with a roller gear perpendicular to the rack gear so that the roller gear is rotatably mounted on the rack gears to allow the rider to make a horizontally reciprocal movement along the rack gears. Preferably, the rider is maintained below the elongated top panel.

The massager further includes a pair of roller coasters provided parallel to each other and attached to the base frame to each have a substantially waved top surface, and a coasting member liftedly engaged between the lifter and the rider where a coaster guide roller is formed outwardly extending from each side surface of the coasting member. The coaster guide roller enables the coasting member to make a roller coasting movement on and along the waved top surfaces of the roller coasters. Elongated guides downwardly extend from the coasting member, and guide bushes are upwardly formed on the rider to releasably receive the elongated guides so as to stabilize the roller coasting movement of the coasting member along the roller coasters and the lifting of the coasting member from the rider.

A gear shaft is rotatably engaged to the massage member and partitioned to first and second halves respectively threaded symmetrical to each other such that the first support carried on the first half either approaches to or distances from the second support carried on the second half of the gear shaft in accordance with a rotating direction of the gear shaft where a first motor connected to the gear shaft to control the rotation of the gear shaft. Also, rider guide rollers are provided on each side of the rider to become rollably engaged in the base frame to guide the horizontally reciprocal movement of the rider. In a better version, the first and second supports repeatedly approach to and distance from each other in perpendicular to the horizontally reciprocal movement of the rider. The vertical reciprocation of the lifter is preferably implemented by a gear-motor application, a gear-chain mechanism or a cam-motor application.

The massage bumps each formed in hemisphere are partitioned to first and second pairs where the first pair massage bumps are formed atop the first support and the second pair massage bumps are formed atop the second support. Here, each pair bumps are aligned parallel to the direction of the rider reciprocation. The massage bumps each include a heater that is a heating lamp generating heat and infrared rays.

A heating member is selectively spread in the top panel of the base frame.

Advantages of the present inventions are numerous. Most of all, the lie-down massager according to the present invention optimally combines a lengthwise reciprocation of massage bumps with a vertically reciprocal movement and with a widthwise reciprocation of the massage bumps for thereby enabling an evenly widespread massaging on the back and neck of a patient lying on the massager.

Further, the combination of the triple reciprocations results in a conspicuous therapeutic effects by realizing a virtually total back massaging while lying on the bed or mat type massager. Also, the massager maximally synthesizes multiple reciprocations in the movement of the massage bumps while relaxing on the bed or mat type massager, thereby enhancing product reliability and customer satisfaction.

Although the present invention is briefly summarized, the full understanding of the invention can be obtained by the following drawings, detailed description and appended claims.

BRIEF DESCRIPTION OF THE DRAWINGS

These and other features, aspects and advantages of the present invention will become better understood with reference to the accompanying drawings, wherein.

DETAILED DESCRIPTION OF THE PREFERRED EMBODIMENTS

Figure 1:
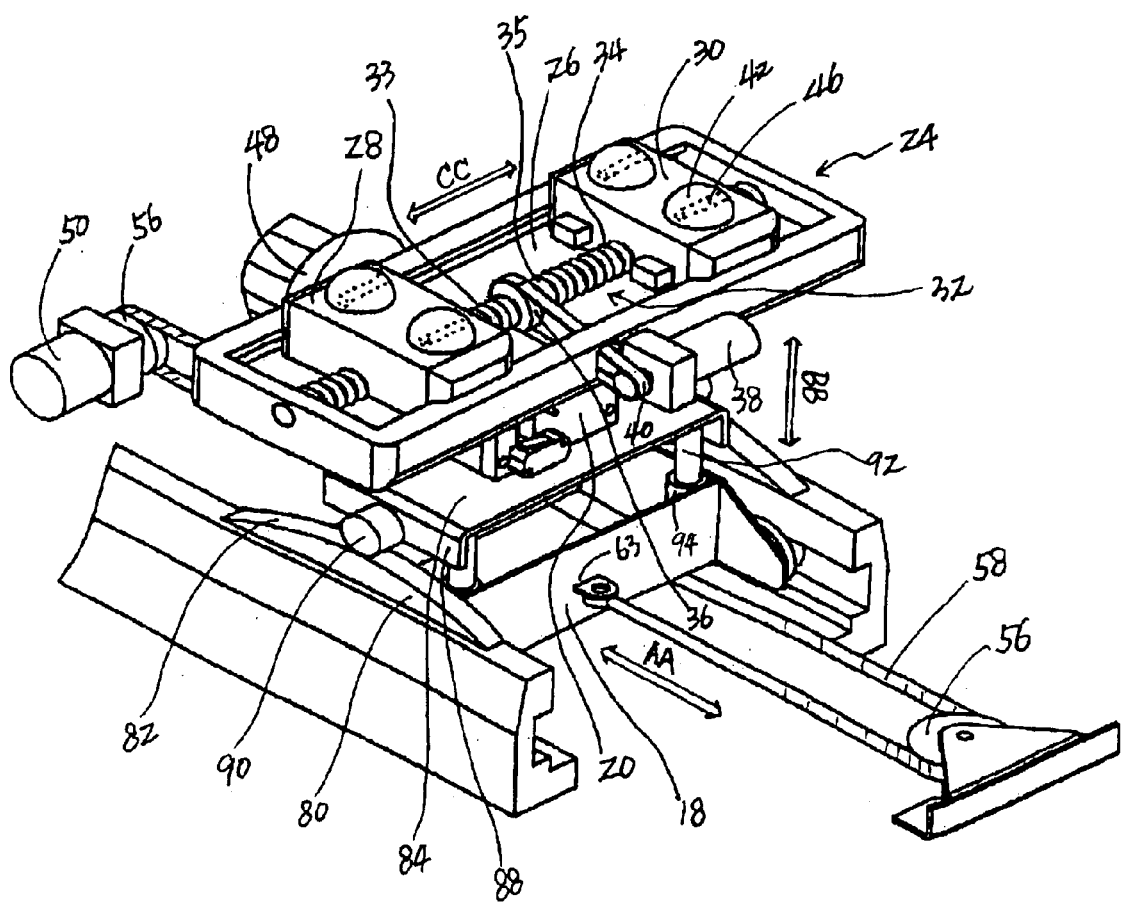
FIG. 1 is a perspective view showing a mechanism of a lie-down massager according to the present invention.
Figure 2:
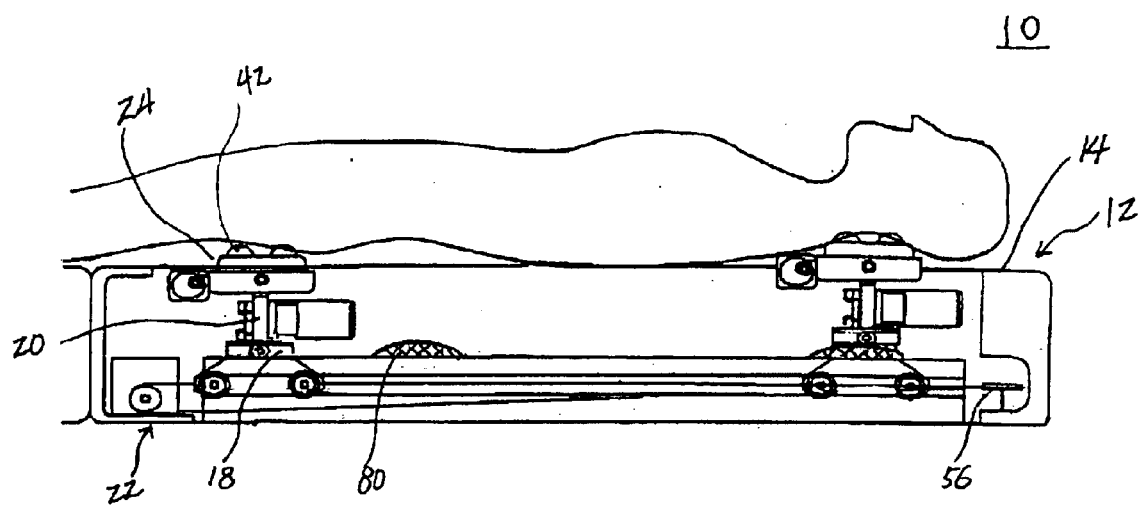
FIG. 2 is a view showing the lie-down massager with a patient lying thereon according to the present invention.
Figure 3:
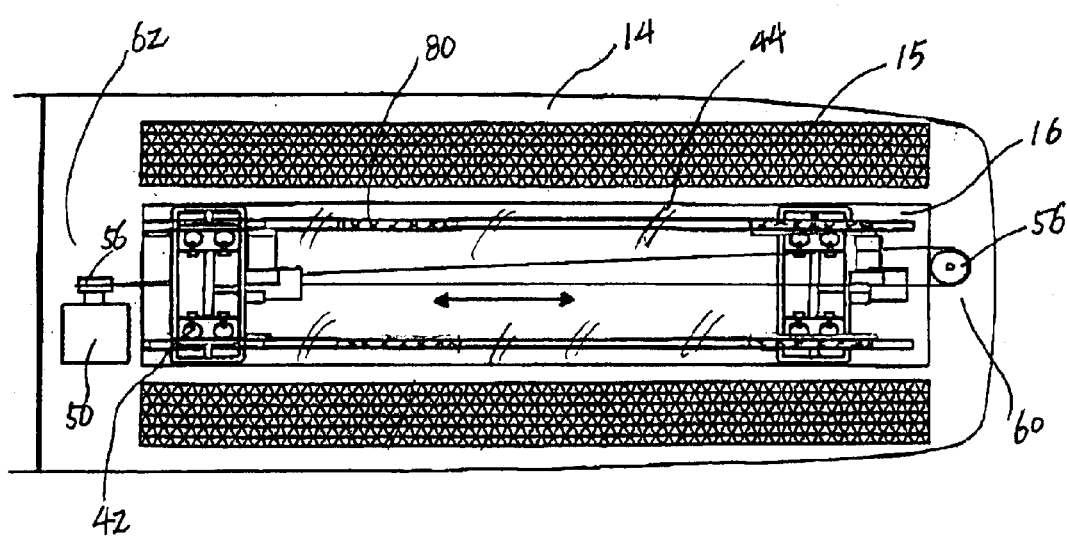
FIG. 3 is a plan view showing the lie-down massager without the patient in FIG. 2.
Figure 4A:
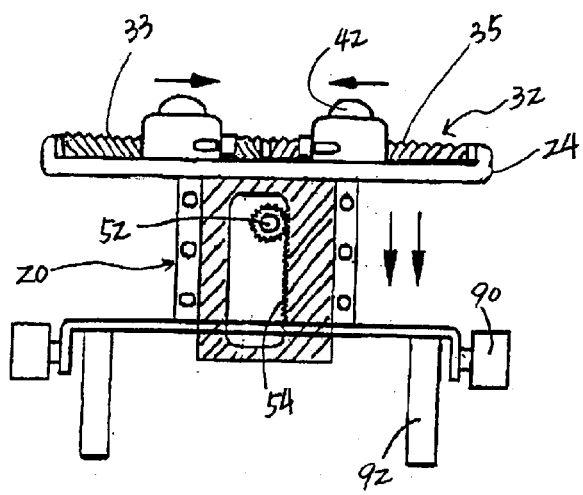
FIGS. 4A–4D are views showing vertical and widthwise reciprocations implemented in the present invention.
Figure 4B:
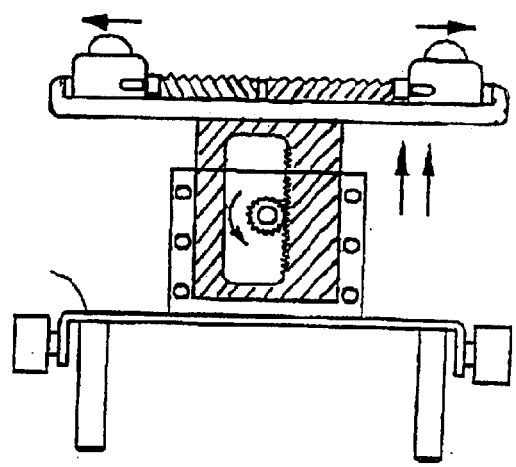
Figure 4C:
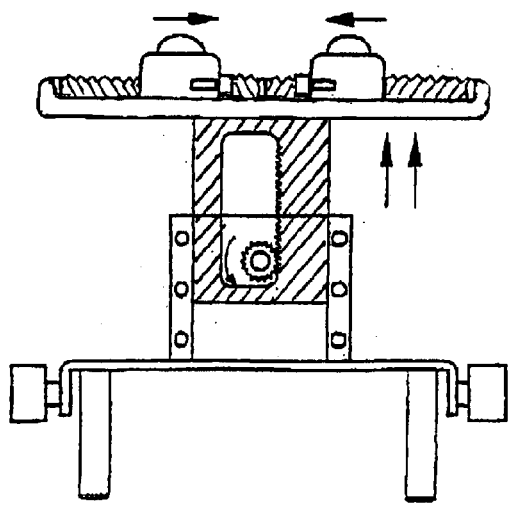
Figure 4D:
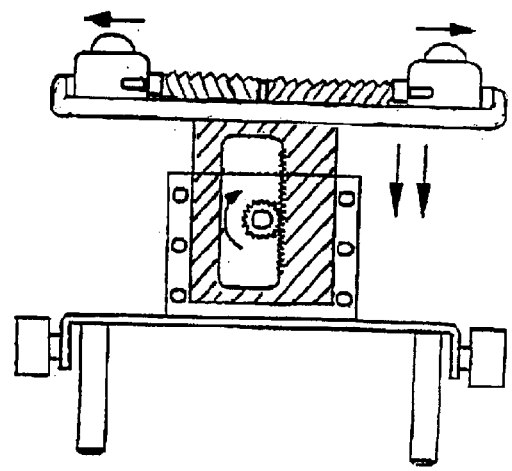

FIG. 1 shows a brief construction of a lie-down massager 10 according to a preferred embodiment of the present invention. FIG. 2 shows the lie-down massager 10 with a patient lying thereon, and FIG. 3 shows a plan view of the massager 10 excluding the patient. As shown therein, the lie-down massager 10 includes a base frame 12 in a bed type or a mat type. The base frame 12 includes an elongated top panel 14 with a heating member 15 spread in the top panel 14 to further comfort the patient on the massager 10. An elongated opening 16 is formed centrally and lengthwisely through the elongated top panel 14. The heating member 15 is preferably formed around the elongated opening 16 to generate heat rays at a predetermined temperature. The massager 10 includes a rider 18 and a lifter 20. The lifter 20 is liftedly engaged to the rider 18 to make a vertically reciprocal movement relative to the rider. The rider 18 is provided below the elongated top panel 14 of the base frame 12 to make a horizontally reciprocal movement relative to the base frame 12. Here, a guide member 22 is movably engaged between the base frame 12 and the rider 18 so as to enable the rider 18 to make a horizontally reciprocal movement along the elongated top panel 14. Here, the guide member 22 may be formed of either a rope-pulley mechanism in FIG. 1 or a rack gear mechanism in FIG. 5.

To improve massaging effects, a massage member 24 is fixed downwardly to the lifter 20. Along a top portion 26 of the massage member 24 are horizontally aligned first and second supports 28, 30. There is also provided a means 32 for allowing the first and second supports 28, 30 to repeatedly approach to and distance from each other within the elongated opening 16. The means 32 includes a gear shaft 34 rotatably engaged to the massage member 24 and partitioned to first and second halves 33, 35 respectively threaded symmetrical to each other by a shaft center 36 such that the first support 28 carried on the first half 33 either approaches to or distances from the second support 30 carried on the second half 35 of the gear shaft 34 in accordance with a rotating direction of the gear shaft 34. The shaft center 36 is connected to a first motor 38 to control the rotation of the gear shaft 34, preferably by a belt 40. The belt 40 may be a timing belt, and the first motor 38 may be a geared motor.

Selectively, the means 32 may be a pinion-rack mechanism where a pinion engaged to a motor controls a relative movement of rack gears connected to the supports 28, 30 so that a bi-directional rotation of the pinion gear enables the supports 28, 30 to repeatedly approach to and distance from each other. The means 32 may also be implemented by adopting a spring restitution for the approaching motion and a gear-motor mechanism for the distancing motion of the supports 28, 30.

In order to implement a therapeutic massage operation, a plurality of massage bumps 42 are attached atop the first and second supports 30. The massage bumps 42 are provided to move along the elongated opening 16 of the elongated top panel 14 of the base frame 12. So the massage bumps 42 are directed to massage the back and neck of the patient lying on the top panel 14 of the base frame 12. Here, a pad 44 may be provided to cover the massage bumps 42 and the elongated opening 16 of the base frame 12. The massage bumps 42 are preferably partitioned to first and second pairs so that the first pair bumps are aligned parallel to the second pair bumps. The massage bumps 42 may each include a heater 46 preferably in form of a heating lamp. Selectively, the heating lamp for the heater 46 may be formed to generate heat and infrared rays to maximize therapeutic effects. In a preferred version, the massage bumps 42 are each formed in hemisphere. Specifically, the massage bumps 42 are partitioned to first and second pairs, wherein the first pair massage bumps are formed atop the first support 28 and the second pair massage bumps are formed atop the second support 30 so that each pair bumps 42 are aligned parallel to the direction of the rider reciprocation.

As shown back in FIG. 1, the massager 10 optimally combines a plurality of reciprocal movements. First, the rider 18 makes a lengthwise reciprocation along the top panel 14, for example, by a pulley mechanism (AA) so that the massage bumps 42 to progressively massage along the back and neck of the patient lying on the massager 10. Second, the rider 20 serves to make a vertical reciprocation (BB) so as to efficiently control the push-up of the massage bumps 42 on the back and neck of the patient, whereby the patient is allowed to optimize the push-up or upward pressure of the massage bumps 42 depending on the patient.

For example, a skinny woman with a back pain feels painful when the massage bumps 42 pushes up or massage her back to an extent in which a masculine man feels appropriate. Third, the massage bumps 42 make a horizontally reciprocal pulsation alternately moving toward or away (CC) from each pair bumps 42 so that the massage bumps 42 become evenly applied to a patient's back portion between the spinal cord and sides. Further, since each of the three reciprocations are motor-powered, the user can easily control each reciprocal operation, for example, by using a hand-held control (not shown). That is, the first and second supports 28, 30 become approached to and distanced from each pair massage bumps 42 in accordance with the first motor 40, the lifer 20 is controlled by a second motor 48, and the rider 18 is controlled by a third motor 50.

Figure 6A:
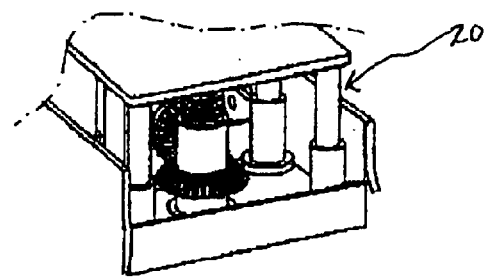
FIGS. 6A–6F are views showing applications of a lifter in the present invention.
Figure 6B:
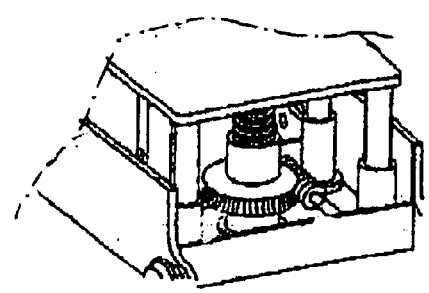
Figure 6C:
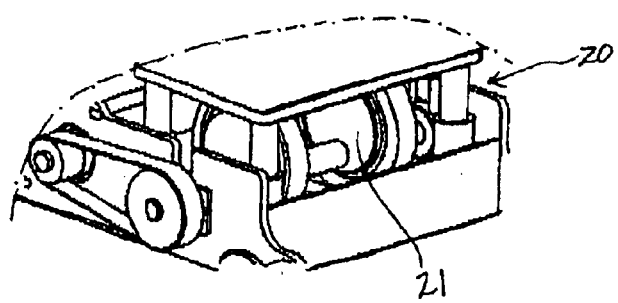
Figure 6D:
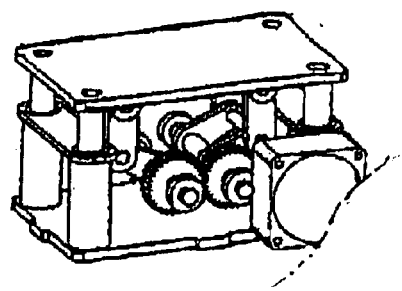
Figure 6E:
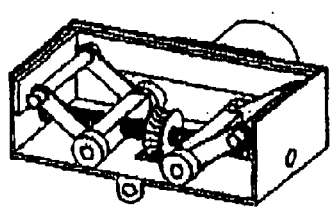
Figure 6F:
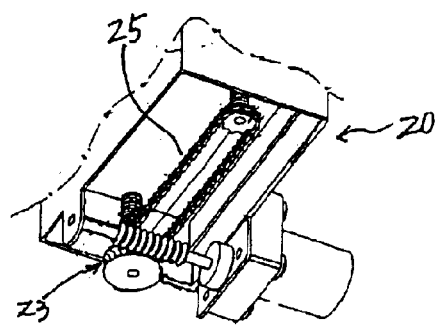

FIGS. 4A–4D respectively show a relative mechanism of the lifter 20 and the massage member 24. As shown therein, while the lifter 20 makes an upward or downward stroke, the first and second supports 28, 30 either approach to or distance from each other depending upon the patient's control. Specifically, the first and second supports 2B, 30 repeatedly approach to and distance from each other in perpendicular to the horizontally reciprocal movement of the rider 18. As an example in FIG. 4A, a roller gear 52 powered by the second motor 48 is engaged to a rack gear 54 to vertically reciprocate the lifter 20. Likewise, in order to implement the vertical reciprocation, the lifter 20 may employ a mechanism selected from a pinion-rack mechanism powered by a motor, a gear-motor application, a gear-chain mechanism powered by a motor, a cam-motor application, and other vertical reciprocation applications as illustrated in FIGS. 6A–6F. That is, FIGS. 6A, 6B and 6E are examples of gear-applied lifter 20, and FIG. 6C employs a cam 21 to generate a vertically reciprocal movement of the lifter 20. FIG. 6F shows the lifter 20 employing a combination of a gear set 23 and a chain 25 for the vertical reciprocation of the lifter 20.

In order to facilitate the lengthwise reciprocation of the rider 16, the guide member 22 may be incorporated in a pair of pulleys 56 linked by a rope 58 and respectively mounted in a front end portion 60 and a rear end portion 62 of the base frame 12. A predetermined portion 63 of the rope 58 is fixedly attached to the rider 18 so that the pulley rotation enables the rider 18 to generate a horizontally reciprocal movement along the elongated top opening 16. There is also provided the pulley motor 50 that controls one of the pulleys 56. In a preferred version, the pulley motor 50 is provided adjacent to the pulley 56 provided in the rear end portion 56 of the base frame 12. Preferably, the pulleys 56 are relatively twisted by 90 degrees against each other to facilitate the horizontal reciprocation of the rider 18.

Figure 5:
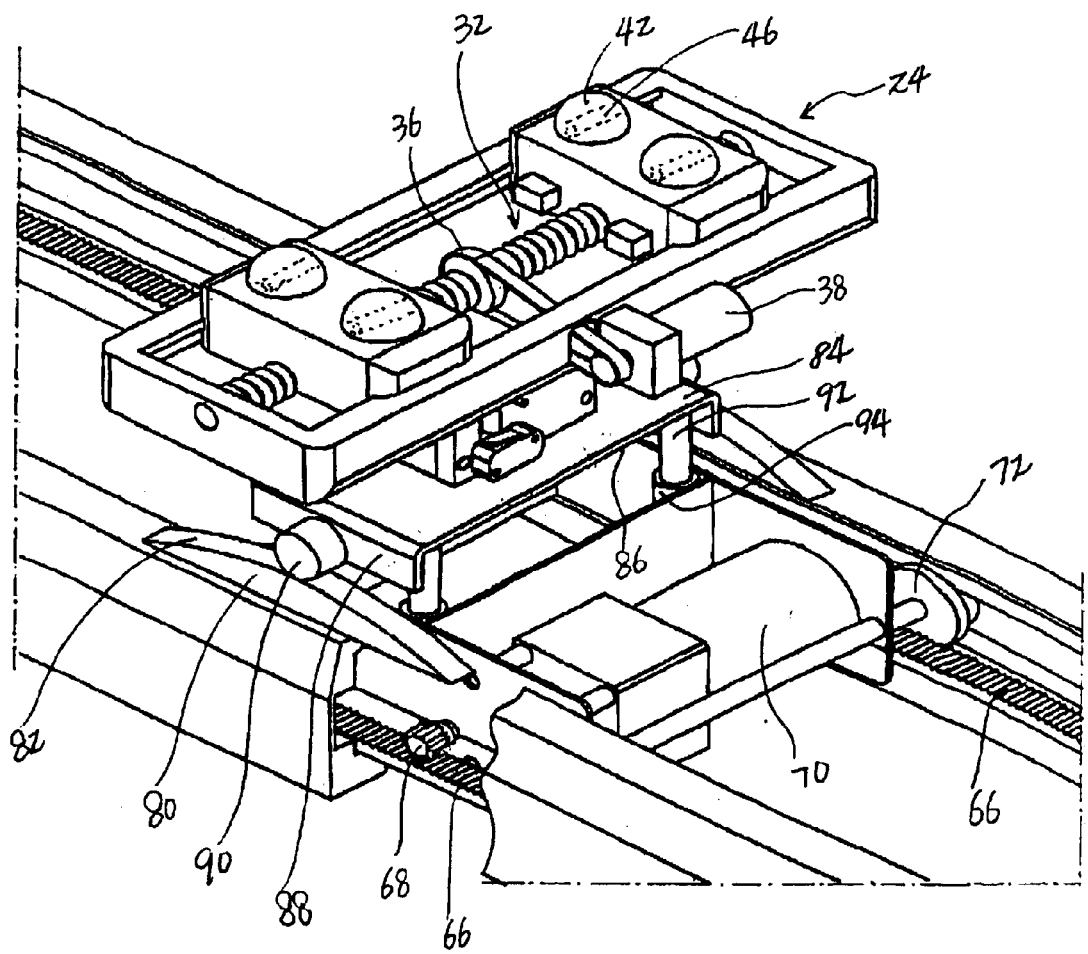
FIG. 5 is a perspective view showing an embodiment of the present invention.

Meanwhile, as shown in FIG. 5, when the guide member 22 is incorporated in the rack gear mechanism, the guide member 22 comprises a pa-r of side rack gears 66 parallel to each other and lengthwisely provided below the elongated top panel 14 of the base frame 12, a roller gear 68 perpendicular to the side rack gears 66, and a motor 70 to power the roller gear 68. Here, the roller gear 68 is rollably connected to the rider 18 and rotatably mounted on the side rack gears 66. In this construction, the roller gear 68 is rotatably mounted on the rack gears 66 to allow the rider 18 to make the horizontal reciprocation along the rack gears 66 where the rider 18 is also maintained below the elongated top panel 14 of the base frame 12. Here, a plurality of guider rollers 72 may be formed from each side of the rider 18 to further stabilize the horizontally reciprocal movement of the rider 18 along the rack gears 66. The roller gear 68 is powered by the second motor 70 fixed to the rider 18.

For a better performance, a pair of roller coasters 80 parallel to each other and to the rack gears 66 are attached to the base frame 12 to allow the horizontally moving rider 18 to pass therebetween. The roller coasters 80 are each formed to have a substantially waved top surface 82. In this construction, a coasting member 84 having a bottom surface 86 and side surfaces 88 is liftedly engaged to the rider 18. In a preferred version, the waved top surfaces 82 of the roller coasters 80 each substantially form a curvature of a human spinal cord. Also, a guide roller 90 is formed outwardly extending from the side surfaces 88 of the coasting member 84. Here, the guide roller 90 on each of the side surfaces 88 enables the coasting member 84 to make a roller coasting movement on and along the waved top surfaces 82 of the roller coasters 80 while being engagedly lifted from the rider 18 which makes the horizontally reciprocal movement. Preferably, the coasting member 84 is formed in a container type. On the other hand, elongated guides 92 are provided extending from the bottom surface 86 of the coasting member 84, and second guide bushes 94 are upwardly formed on the rider 18 to releasably receive the second elongated guides 92 so as to stabilize the roller coasting movement of the coasting member 84 along the roller coasters 80 and the lifting of the coasting member 84 from the rider 18.

As discussed above, an advantage of the present inventions is that the lie-down massager 10 according to the present invention optimally combines a lengthwise reciprocation of massage bumps 42 with a vertically reciprocal movement and with a widthwise reciprocation of the massage bumps 42 for thereby enabling an evenly widespread massaging on the back and neck of a patient lying on the massager.

In addition, the combination of the triple reciprocations substantially alleviate pains resulting from the conventional massager using a predetermined solid pattern along which the rider 18 follows without a vertically allowable resilience, thereby improving product reliability. Further, the coasting member 84 working with the roller coasters 80 to realize an additional lifting by utilizing the horizontally reciprocal movement of the rider 18 enables the massaging bumps 32 to continue a smooth, steady and robust massaging on the patient together with the triple reciprocations, thereby substantially improving massaging effect and subsequently maximizing customer satisfaction.

Although the invention has been described in considerable detail, other versions are possible by converting the aforementioned construction. Therefore, the scope of the invention shall not be limited by the specification specified above and the appended claims.

What is claimed is:

1. A lie-down massager, comprising:
   a) a base frame having an elongated top panel, wherein an elongated top opening is formed centrally and lengthwisely through the elongated top panel;
   b) a rider provided below the elongated top panel of the base frame to make a horizontally reciprocal movement relative to the base frame;
   c) a lifter liftedly engaged to the rider to make a vertically reciprocal movement relative to the rider;
   d) a massage member fixed downwardly to the lifter, wherein first and second supports are horizontally aligned along a top portion of the massage member;
   e) means for allowing the first and second supports to repeatedly approach to and distance from each other within the elongated opening;
   f) massage bumps attached atop the first and second supports; and
   g) a pad covering the massage bumps and the elongated opening of the base frame.

2. The lie-down massager of claim 1 wherein the means comprises:
   a) a gear shaft rotatably engaged to the massage member and partitioned to first and second halves respectively threaded symmetrical to each other such that the first support carried on the first half either approaches to or distances from the second support carried on the second half of the gear shaft in accordance with a rotating direction of the gear shaft; and
   b) a first motor connected to the gear shaft to control the rotation of the gear shaft.

3. The lie-down massager of claim 2 wherein the first and second supports repeatedly approach to and distance from each other in perpendicular to the horizontally reciprocal movement of the rider.

4. The lie-down massager of claim 1 wherein the vertical reciprocation of the lifter is implemented by a gear-motor application.

5. The lie-down massager of claim 1 wherein the vertical reciprocation of the lifter is implemented by a gear-chain mechanism powered by a second motor.

6. The lie-down massager of claim 1 wherein the vertical reciprocation of the lifter is implemented by a cam-motor application.

7. The lie-down massager of claim 1 wherein the massage bumps are each formed in hemisphere.

8. The lie-down massager of claim 1 wherein the massage bumps are partitioned to first and second pairs, wherein the first pair massage bumps are formed atop the first support and the second pair massage bumps are formed atop the second support, wherein said each pair bumps are aligned parallel to the direction of the rider reciprocation.

9. The lie-down massager of claim 1 wherein the massage bumps each include a heater, wherein the heater is a heating lamp generating heat and infrared rays.

10. The lie-down massager of claim 1 further comprising a heating member spread in the top panel of the base frame.

11. A lie-down massager, comprising:
   a) a base frame having an elongated top panel, wherein an elongated top opening is formed centrally and lengthwisely through the elongated top panel;
   b) a rider provided below the elongated top panel;
   c) a pair of pulleys linked by a rope and respectively mounted in a front end portion and a rear end portion of the base frame, wherein a predetermined portion of the rope is fixedly attached to the rider so that the pulley rotation enables the rider to generate a horizontally reciprocal movement along the elongated top opening;
   d) a lifter liftedly engaged to the rider to make a vertically reciprocal movement relative to the rider;
   e) a massage member fixed downwardly to the lifter, wherein first and second supports are horizontally aligned along a top portion of the massage member;
   f) means for allowing the first and second supports to repeatedly approach to and distance from each other within the elongated opening;
   g) massage bumps attached atop the first and second supports; and
   h) a pad covering the massage bumps and the elongated opening of the base frame.

12. The lie-down massager of claim 11 further comprising:
   a) a pair of roller coasters parallel to each other and attached to the base frame, wherein the roller coasters each have a substantially waved top surface; and
   b) a coasting member liftedly engaged between the lifter and the rider, wherein a coaster guide roller is formed outwardly extending from each side surface of the coasting member, wherein the coaster guide roller enables the coasting member to make a roller coasting movement on and along the waved top surfaces of the roller coasters.

13. The lie-down massager of claim 12 further comprises:
   a) elongated guides downwardly extending from the coasting member; and
   b) guide bushes upwardly formed on the rider to releasably receive the elongated guides so as to stabilize the roller coasting movement of the coasting member along the roller coasters and the lifting of the coasting member from the rider.

14. The lie-down massager of claim 11 wherein the means comprises:
   a) a gear shaft rotatably engaged to the massage member and partitioned to first and second halves respectively threaded symmetrical to each other such that the first support carried on the first half either approaches to or distances from the second support carried on the second half of the gear shaft in accordance with a rotating direction of the gear shaft; and
   b) a first motor connected to the gear shaft to control the rotation of the gear shaft.

15. The lie-down massager of claim 11 further comprises rider guide rollers on each side of the rider, wherein the rider guide rollers are rollably engaged in the base frame to guide the horizontally reciprocal movement of the rider.

16. The lie-down massager of claim 11 wherein the waved top surfaces of the roller coasters each substantially form a curvature of a human spinal cord.

17. The lie-down massager of claim 11 wherein the first and second supports repeatedly approach to and distance from each other in perpendicular to the horizontally reciprocal movement of the rider.

18. The lie-down massager of claim 11 wherein the vertical reciprocation of the lifter is implemented by a gear-motor application.

19. The lie-down massager of claim 11 wherein the vertical reciprocation of the lifter is implemented by a gear-chain mechanism powered by a second motor.

20. The lie-down massager of claim 11 wherein the vertical reciprocation of the lifter is implemented by a cam-motor application.

21. The lie-down massager of claim 11 wherein the massage bumps are each formed in hemisphere.

22. The lie-down massager of claim 11 wherein the massage bumps are partitioned to first and second pairs, wherein the first pair massage bumps are formed atop the first support and the second pair massage bumps are formed atop the second support, wherein said each pair bumps are aligned parallel to the direction of the rider reciprocation.

23. The lie-down massager of claim 11 wherein the massage bumps each include a heater, wherein the heater is a heating lamp generating heat and infrared rays.

24. The lie-down massager of claim 11 further comprising a heating member spread in the top panel of the base frame.

* * * * *